(12) United States Patent
Cai et al.

(10) Patent No.: US 7,504,382 B2
(45) Date of Patent: Mar. 17, 2009

(54) PROTEASE INHIBITORS FOR CORONAVIRUSES AND SARS-COV AND THE USE THEREOF

(75) Inventors: Sui Xiong Cai, San Diego, CA (US); William E. Kemnitzer, Irvine, CA (US); Hong Zhang, San Diego, CA (US); Han-Zhong Zhang, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 54 days.

(21) Appl. No.: 10/839,753

(22) Filed: May 6, 2004

(65) Prior Publication Data

US 2008/0300191 A1     Dec. 4, 2008

Related U.S. Application Data

(60) Provisional application No. 60/551,362, filed on Mar. 10, 2004, provisional application No. 60/536,701, filed on Jan. 16, 2004, provisional application No. 60/512,845, filed on Oct. 21, 2003, provisional application No. 60/470,881, filed on May 16, 2003, provisional application No. 60/468,098, filed on May 6, 2003.

(51) Int. Cl.
    *A61K 38/00* (2006.01)
(52) U.S. Cl. ........................................... 514/19
(58) Field of Classification Search .................... 514/19
    See application file for complete search history.

(56) References Cited

U.S. PATENT DOCUMENTS

| | | | |
|---|---|---|---|
| 4,665,070 A * | 5/1987 | Krantz et al. ............. | 514/230.5 |
| 6,153,591 A | 11/2000 | Cai et al. | |
| 6,184,210 B1 | 2/2001 | Keana et al. | |
| 6,315,995 B1 * | 11/2001 | Pinsky et al. ............. | 424/94.63 |
| 6,355,618 B1 | 3/2002 | Cai et al. | |
| 6,495,522 B1 | 12/2002 | Wang et al. | |
| 6,534,530 B1 * | 3/2003 | Dragovich et al. .......... | 514/365 |
| 6,566,338 B1 | 5/2003 | Weber et al. | |
| 6,596,693 B1 | 7/2003 | Keana et al. | |
| 6,620,782 B1 | 9/2003 | Cai et al. | |
| 6,632,962 B2 | 10/2003 | Golec et al. | |
| 6,716,818 B2 | 4/2004 | Cai et al. | |
| 6,716,859 B2 | 4/2004 | Cai et al. | |
| 6,794,400 B2 | 9/2004 | Cai et al. | |
| 6,949,516 B2 | 9/2005 | Keana et al. | |
| 6,984,718 B2 | 1/2006 | Zhang et al. | |
| 2003/0181388 A1 | 9/2003 | Cai et al. | |
| 2003/0208037 A1 | 11/2003 | Zhang et al. | |
| 2004/0116355 A1 | 6/2004 | Cai et al. | |
| 2004/0186078 A1 | 9/2004 | Cai et al. | |
| 2005/0192231 A1 | 9/2005 | Keana et al. | |

FOREIGN PATENT DOCUMENTS

JP           05-117169      *   5/1993

OTHER PUBLICATIONS

Brandt W, Lehmann T, Willkomm C, Fittkau S, Barth A., "CoMFA investigations on two series of artificial peptide inhibitors of the serine protease thermitase. Synthesis of an inhibitor of predicted greater potency," Int J Pept Protein Res. Jul. 1995;46(1):73.*

Webber SE, et al, "Tripeptide aldehyde inhibitors of human rhinovirus 3C protease: design, synthesis, biological evaluation, and cocrystal structure solution of P1 glutamine isosteric replacements," J Med Chem. Jul. 16, 1998;41(15):2786-805.*

Morris, Tina S, et al, "In vitro and ex vivo inhibition of hepatitis A virus 3C proteinase by a peptidyl monofluoromethyl ketone," Bioorganic & Medicinal Chemistry (1997), 5(5), 797-807.*

Morris, Tina S, et al., "In vitro and ex vivo inhibition of hepatitis A virus 3C proteinase by a peptidyl monofluoromethyl ketone," Bioorganic & Medicinal Chemistry (1997), 5(5), 11191-11197.*

STN search report—two pages.*

Anand, K., et al., "Coronavirus Main Proteinase ($3CL^{pro}$) Structure: Basis for Design of anti-SARS Drugs," *Science* 300:1763-1767, Supplemental Material pp. 1-13, American Association for the Advancement of Science (Jun. 2003).

Anand, K., et al., "Coronavirus Main Proteinase ($3CL^{pro}$) Structure: Basis for Design of anti-SARS Drugs," *Scienceexpress* pp. 1-6, Supplemental Material pp. 1-4, American Association for the Advancement of Science (May 13, 2003).

Matthews, D.A., et al., "Structure-assisted design of mechanism-based irreversible inhibitors of human rhinovirus 3C protease with potent antiviral activity against multiple rhinovirus serotypes," *Proc. Natl. Acad. Sci. USA* 96:11000-11007, The National Academy of Sciences (1999).

Patick, A.K., et al., "In Vitro Antiviral Activity of AG7088, a Potent Inhibitor of Human Rhinovirus 3C Protease," *Antimicrob. Agents Chemother.* 43:2444-2450, American Society for Microbiology (1999).

Mertz, P., Office Action for U.S. Appl. No. 11/100,470, U.S. Patent and Trademark Office, Alexandria, Virginia, mailed Jul. 16, 2007.

Kudla, J. S., Office Action for U.S. Appl. No. 10/510,104, U.S. Patent and Trademark Office, Alexandria, Virginia, mailed Dec. 19, 2007.

Mertz, P. M.., Office Action for U.S. Appl. No. 11/100,470, U.S. Patent and Trademark Office, Alexandria, Virginia, mailed Nov. 2, 2007.

* cited by examiner

*Primary Examiner*—Cecilia Tsang
*Assistant Examiner*—Thomas S Heard
(74) *Attorney, Agent, or Firm*—Sterne, Kessler, Goldstein & Fox P.L.L.C.

(57) ABSTRACT

Disclosed are protease inhibitors for coronaviruses and SARS-CoV, or picornaviruses, and the use of these protease inhibitors for preventing, reducing, ameliorating and treating a disease or condition caused by coronaviruses and SARS-CoV, or picornaviruses. Also disclosed are methods of reducing or preventing the spread of coronavirus, or picornaviruses, and preventing or reducing the replication of coronavirus, or picornaviruses, with the compounds of the present invention.

1 Claim, No Drawings

PROTEASE INHIBITORS FOR CORONAVIRUSES AND SARS-COV AND THE USE THEREOF

BACKGROUND OF THE INVENTION

1. Field of the Invention

This invention is in the field of medicinal chemistry. In particular, the invention relates to protease inhibitors for coronaviruses and SARS-CoV, or picornaviruses. The invention also relates to the use of these protease inhibitors for ameliorating or treating disease that was caused by coronaviruses and SARS-CoV, as well as picornaviruses.

2. Prior Art

The causative pathogen of severe acute respiratory syndrome (SARS) has been identified as a virus of the coronavirus family (Peiris J. et al. Lancet, 2003, 361: 1319-1325). Coronaviruses are positive-stranded RNA viruses with large genome sizes and are known to be responsible for diseases in animals and in humans. There are two coronaviruses, HCV OC43 and HCV 229E, that are known to be the cause of some common colds. The molecular biology of these coronaviruses has been studies and there is a good understanding of the structure and function of the genes and proteins of these viruses (Lai, M. M. C. and Cavanagh, D. Adv. Virus Res. 1997, 48: 1-100). Coronaviruses are known to encode several proteases that process the virus proteins and these proteases are essential for the replication of the viruses (Ziebuhr J. et al. J. Gen. Virol. 2000, 81: 853-79). These proteases have been found to be cysteine proteases, including $PL1^{pro}$ and $PL2^{pro}$ that are papain-like protease, and are analogous to the foot and mouth disease virus leader protease, $L^{pro}$, as well as the main $3CL^{pro}$ that is a chymotrypsin-like protease, and is analogous to the main picornavirus protease, $3C^{pro}$. The conservation of substrate specificities among the main proteases $3CL^{pro}$ of coronaviruses has been reported, with LQS or LQA as the preferred P2-P1-P1' sequences (Hegyi A. and Ziebuhr J. J. Gen. Virol. 2002, 83: 595-9; and Hegyi, A. et al. J. Gen. Virol. 2002, 83: 581-593). The genome of the new coronavirus that cause severe acute respiratory syndrome (SARS-CoV) has been determined by several groups (Ksiazek, T. et al. N. Engl. J. Med. 2003, 348: 1953-1966; and Drosten, C. et al. N. Engl. J. Med. 2003, 348: 1967-76). It is reported that although the overall gene products of ORF1a are poorly conserved among different coronaviruses, the protease sequences are the exceptions. The predicted gene product of ORF1a of SARs-CoV appears to contain one $PLP^{pro}$ domain. The $3CL^{pro}$ catalytic histidine and cysteine residue are fully conserved among all coronaviruses including SARS-CoV ($His_{3281}$ and $Cys_{3385}$) (Rota P. et al., Scienceexpress, 2003, 300: 1394-1399). In addition, it is reported that the replicase 1a and 1b ORFs of SARS-CoV occupy 21.2 kb of the SARS virus genome. The genes encode a number of proteins that are produced by proteolytic cleavage of a large polyprotein, which is conserved in both length and amino acid sequence to other coronavirus replicase proteins (Marra M. A. et al., Scienceexpress, 2003, 300: 1399-1404). These results suggested that the protease of SARS-CoV should process the viral protein similar to other coronaviruses.

The proteases of coronaviruses are essential for the processing of viral proteins and replication of the viruses. It has been reported that a cysteine protease inhibitor E64d inhibited the posttranslational processing of viral protein and the replication of the viruses (Kim, J. C. et al. Virology, 1995, 208: 1-8). Therefore the design and synthesis of protease inhibitors of SARS-CoV, and coronaviruses, could lead to effective treatment for SARS, as well as effective treatment for other disease that were caused by the coronaviruses in animals and humans.

The protease inhibitor of SARS-CoV and coronaviruses can be designed based on the known conservation of substrate sequence of coronaviruses, and preferably using a dipeptide scaffold. The dipeptide scaffold approach has been used successful in the design of potent and efficacious inhibitors of caspases, another class of cysteine protease important for apoptosis (U.S. Pat. No. 6,184,210). The dipeptide scaffold can be LQ, which is conserved among the main proteases $3CL^{pro}$ of coronaviruses. The dipeptide scaffold also can be RG or RA, which are preferred and conserved for the $PL1^{pro}$ of coronaviruses (Dong, S., Baker, S. C. Virology, 1994, 204: 541-9; and Hughes S. A. et al. J. Virol. 1995, 69: 809-13).

Picornaviruses, another class of RNA viruses, also encode a viral 3C protease for the processing and release of viral proteins, which are essential for the replication of the viruses. The Picornaviruses family are divided into 6 subgroups with similar genetic organization and translation strategies. These subgroups include several important human and veterinary pathogens, such as poliovirus and coxsackievirus (Enterovirus), foot-and mouth disease virus (Aphthovirus), encephalomyocarditis virus (Cardiovirus), hepatitis A virus (Hepatovirus), and human rhinoviruses (Rhinovirus). The crystal structures of several picornavirus 3C proteases have been determined, including type 14 human rhinovirus (Matthews, D. A. et al. Cell, 1994, 77: 761-771), hepatitis A (Allaire, M. et al. Nature (London), 1994, 369: 72-76) and poliovirus (Mosimann, S. C. et al. J. Mol. Biol. 1997, 273: 1032-1047). Picornaviral 3C proteases are a unique class of enzymes with an unusual specificity for Gln-Gly cleavage of its substrates (Matthews, D. A et al. Proc. Natl. Acad. Sci. USA, 1999, 96: 11000-11007). This specificity for Gln-Gly cleavage of substrates is similar to that of the main protease $3CL^{pro}$ ($M^{pro}$) of coronaviruses (Anand, Science, 2003, 300: 1763-1767). Therefore it is expected that protease inhibitor of SARS-CoV and coronaviruses of this invention also should be active as inhibitors of picornaviral 3C proteases, and will be useful for the treatment of diseases that were caused by picornaviruses.

SUMMARY OF THE INVENTION

The invention provides compounds having Formulae I-X as described herein. These compounds are inhibitors of the proteases of SARS-CoV and coronaviruses, or picornaviruses.

The present invention also provides pharmaceutical compositions comprising a compound of Formulae I-X in an effective amount to treat disease caused by SARS-CoV, and coronaviruses, or picornaviruses in an animal.

The invention also relates to the use of the compounds of the invention for ameriolating, preventing or treating conditions in which SARS-CoV, and coronaviruses, or picornaviruses is a causative factor.

The invention also provides methods for preventing or reducing the spread of coronavirus, or picornaviruses, comprising contacting an article or waste suspected of being contaminated with a coronavirus with a compound of the present invention.

The invention also provides methods for preventing or reducing the replication of coronavirus, or picornaviruses, comprising contacting the coronavirus with a compound of the present invention.

DETAILED DESCRIPTION OF THE INVENTION

The inhibitors of proteases of SARS-CoV and coronaviruses of the present invention include compounds having the general Formula (X):

(X)

$R_5$—A—L—NH—CH(Y)—C(O)—$R_2$ wherein Y is a hydrogen, alkyl, $CH_2(CH_2)_nC(O)NR_1R_3$ or $CH_2(CH_2)_nNR_{16}C(O)NR_1R_3$;

wherein n is 0-2;

wherein $R_1$ and $R_3$ are independently hydrogen or an optionally substituted alkyl; or $R_1$ and $R_3$, together with the nitrogen to which $R_1$ and $R_3$ are attached form a heterocycle;

wherein $R_{16}$ is hydrogen or an optionally substituted alkyl; or $R_{16}$, with one of the $R_1$ or $R_3$, together with the attached atoms, form a heterocycle;

wherein $R_2$ is hydrogen or optionally substituted alkyl;

wherein L is a bond, or —$ZCR_6R_7C(O)$—;

wherein $R_6$ and $R_7$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

wherein Z is a bond, an oxygen, —$CR_8R_9$—, or a structure given by the following formula:

(XI)

wherein $R_8$ and $R_9$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

wherein $R_{10}$ and $R_{11}$ independently are hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

wherein X is $CR_{17}$ or N, wherein $R_{17}$ is hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

wherein A is a peptide of 1-2 amino acids or a bond;

wherein $R_5$ is a group including one of the following structures:

(IVa)

(IVb)

(IVc)

(VIIIa)

(VIIIb)

(VIIIc)

(VIIId)

wherein $R_4$ is optionally substituted alkyl, optionally substituted alkoxy, optionally substituted benzyloxy, optionally substituted aryloxy, optionally substituted arylalkyloxy, optionally substituted alkylamine, optionally substituted benzylamine, optionally substituted arylamine, optionally substituted arylalkylamine, optionally substituted carbocyclic, optionally substituted heterocyclic, optionally substituted aryl or optionally substituted heteroaryl; and wherein $R_{12}$, $R_{13}$, $R_{14}$ and $R_{15}$ independently are hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{12}$ and $R_{13}$, $R_{13}$ and $R_{14}$, $R_{14}$ and $R_{15}$, taken together with the atoms to which they are attached, form an aryl, heteroaryl, optionally substituted carbocyclic or optionally substituted heterocyclic group, wherein said group is optionally substituted.

In one embodiment, the inhibitors of proteases of SARS-CoV and coronaviruses of the present invention are compounds having the general Formula I-III:

(I)

(II)

(III)

or pharmaceutically acceptable salts or prodrugs thereof, wherein $R_1$ and $R_3$ are independently hydrogen or an optionally substituted alkyl; or $R_1$ and $R_3$, together with the nitrogen to which $R_1$ and $R_3$ are attached form a heterocycle;

$R_2$ is hydrogen or optionally substituted alkyl;

$R_4$ is optionally substituted alkyl, optionally substituted alkoxy, optionally substituted benzyloxy, optionally substituted aryloxy, optionally substituted arylalkyloxy, optionally substituted alkylamine, optionally substituted benzylamine, optionally substituted arylamine, optionally substituted arylalkylamine, optionally substituted carbocyclic, optionally substituted heterocyclic, optionally substituted aryl or optionally substituted heteroaryl;

A is a peptide of 1-2 amino acids or a bond.

In another embodiment, the inhibitors of proteases of SARS-CoV and coronaviruses of the present invention are compounds having the general Formula IV:

(IV)

or pharmaceutically acceptable salts or prodrugs thereof, wherein n is 0, 1 or 2;

$R_1$ and $R_3$ are independently hydrogen or an optionally substituted alkyl; or $R_1$ and $R_3$, together with the nitrogen to which $R_1$ and $R_3$ are attached form a heterocycle;

$R_2$ is hydrogen or optionally substituted alkyl;

A is a peptide of 1-2 amino acids or a bond;

$R_5$ is a protecting group for the peptide or amino acid. Preferred protecting groups include one of the following structures:

(IVa)

(IVb)

(IVc)

wherein, $R_4$ is optionally substituted alkyl, optionally substituted alkoxy, optionally substituted benzyloxy, optionally substituted aryloxy, optionally substituted arylalkyloxy, optionally substituted alkylamine, optionally substituted benzylamine, optionally substituted arylamine, optionally substituted arylalkylamine, optionally substituted carbocyclic, optionally substituted heterocyclic, optionally substituted aryl or optionally substituted heteroaryl.

In another embodiment, the inhibitors of proteases of SARS-CoV and coronaviruses of the present invention are compounds having the general Formula V:

(V)

or pharmaceutically acceptable salts or prodrugs thereof, wherein n is 0, 1 or 2;

$R_1$ and $R_3$ are independently hydrogen or an optionally substituted alkyl; or $R_1$ and $R_3$, together with the nitrogen to which $R_1$ and $R_3$ are attached form a heterocycle;

$R_2$ is a hydrogen or an optionally substituted alkyl;

$R_6$ and $R_7$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

A is a peptide of 1-2 amino acids or a bond;

$R_5$ is a protecting group for the peptide or amino acid or hydroxy acid as defined with respect to formula IV.

In another embodiment, the inhibitors of proteases of SARS-CoV and coronaviruses of the present invention are compounds having the general Formula VI:

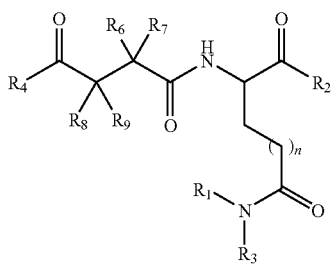

(VI)

or pharmaceutically acceptable salts or prodrugs thereof, wherein n is 0, 1 or 2;

$R_1$ and $R_3$ are independently hydrogen or an optionally substituted alkyl; or $R_1$ and $R_3$, together with the nitrogen to which $R_1$ and $R_3$ are attached form a heterocycle;

$R_2$ is hydrogen or optionally substituted alkyl;

$R_4$ is optionally substituted alkyl, optionally substituted alkoxy, optionally substituted benzyloxy, optionally substituted aryloxy, optionally substituted arylalkyloxy, optionally substituted alkylamine, optionally substituted benzylamine, optionally substituted arylamine, optionally substituted arylalkylamine, optionally substituted carbocyclic, optionally substituted heterocyclic, optionally substituted aryl or optionally substituted heteroaryl;

$R_6$, $R_7$, $R_8$ and $R_9$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl.

In another embodiment, the inhibitors of proteases of SARS-CoV and coronaviruses of the present invention are compounds having the general Formula VII:

(VII)

or pharmaceutically acceptable salts or prodrugs thereof, wherein n is 0, 1 or 2;

$R_1$ and $R_3$ are independently hydrogen or an optionally substituted alkyl; or $R_1$ and $R_3$, together with the nitrogen to which $R_1$ and $R_3$ are attached form a heterocycle;

$R_2$ is hydrogen or optionally substituted alkyl;

$R_5$ is a protecting group for the amino group as defined with respect to formula IV;

$R_6$ and $R_7$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

$R_{10}$ and $R_{11}$ independently are hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

X is $CR_{17}$ or N, wherein $R_{17}$ is hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol.

In another embodiment, the inhibitors of proteases of SARS-CoV and coronaviruses of the present invention are compounds having the general Formula VIII:

(VIII)

or pharmaceutically acceptable salts or prodrugs thereof, wherein n is 0, 1 or 2;

$R_1$ and $R_3$ are independently hydrogen or an optionally substituted alkyl; or $R_1$ and $R_3$, together with the nitrogen to which $R_1$ and $R_3$ are attached form a heterocycle;

$R_2$ is hydrogen or optionally substituted alkyl;

$R_6$ and $R_7$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl; and $R_5$ is a ring structure including one of the following:

(VIIIa)

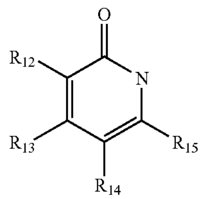

(VIIIb)

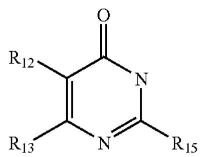

(VIIIc)

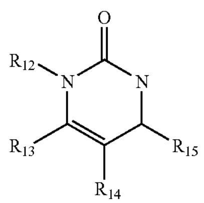

(VIIId)

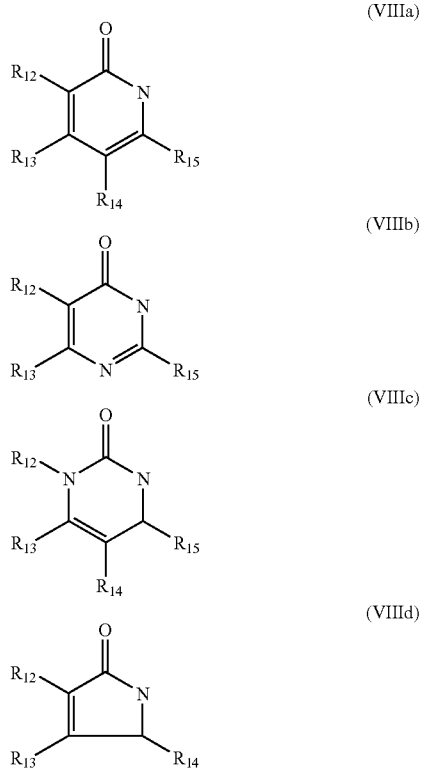

wherein, $R_{12}$, $R_{13}$, $R_{14}$ and $R_{15}$ independently are hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{12}$ and $R_{13}$, $R_{13}$ and $R_{14}$, $R_{14}$ and $R_{15}$, taken together with the atoms to which they are attached, form an aryl, heteroaryl, optionally substituted carbocyclic or optionally substituted heterocyclic group, wherein said group is optionally substituted.

For example, $R_{12}$ and $R_{13}$, $R_{13}$ and $R_{14}$, $R_{14}$ and $R_{15}$, may be taken together to form a structure selected from the group consisting of $OCH_2O—$, $—(CH_2)_3—$, $—(CH_2)_4—$, $—OCH_2CH_2O—$, $—CH_2N(R)CH_2—$, $—CH_2CH_2N(R)CH_2—$, $CH_2N(R)CH_2CH_2—$, —CH═CH—CH═CH—, —N(R)—CH═CH—, —CH═CH—N(R)—, —O—CH═CH—, —CH═CH—O—, —S—CH═CH—, —CH═CH—S—, —N═CH—CH═CH—, —CH═N—CH═CH—, —CH═CH—N═CH—, —CH═CH—CH═N— and —N═CH—CH═N—, wherein R is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

In another embodiment, the inhibitors of proteases of SARS-CoV and coronaviruses of the present invention are compounds having the general Formula IX:

IX

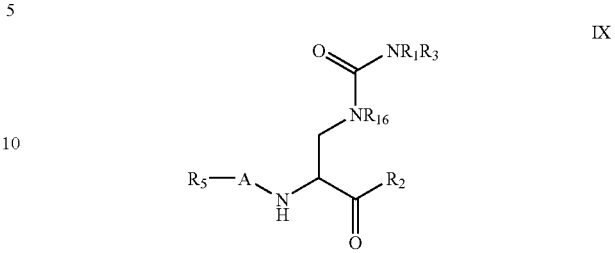

or pharmaceutically acceptable salts or prodrugs thereof, wherein $R_2$ is hydrogen or optionally substituted alkyl;

A is a peptide of 1-2 amino acids or a bond;

$R_5$ is a protecting group for the peptide or amino acid;

$R_1$ and $R_3$ are independently hydrogen or an optionally substituted alkyl; or $R_1$ and $R_3$, together with the nitrogen to which $R_1$ and $R_3$ are attached form a heterocycle;

$R_{16}$ is hydrogen or an optionally substituted alkyl; or $R_{16}$, with one of the $R_1$ or $R_3$, together with the attached atoms, to form a heterocycle.

Preferred A is an amino acid. Examples of one or two amino acids that may make up the peptide A include any one of the common 20 amino acids e.g., Ala, Val, Leu, Ile, Pro, Phe, Trp, Met, Gly, Ser, Thr, Cys, Tyr, Asp, Asn, Glu, Asn, Lys, Arg and His, or non-natural amino acids such as 2-methylvaline, 2-methylalanine, (2-i-propyl)-β-alanine, phenylglycine, 4-methylphenylglycine, 4-isopropylphenylglycine, 3-bromophenylglycine, 4-bromophenylglycine, 4-chlorophenylglycine, 4-methoxyphenylglycine, 4-ethoxyphenylglycine, 4-hydroxyphenylglycine, 3-hydroxyphenylglycine, 3,4-dihydroxyphenylglycine, 3,5-dihydroxyphenylglycine, 2,5-dihydrophenylglycine, 2-fluorophenylglycine, 3-fluorophenylglycine, 4-fluorophenylglycine, 2,3-difluorophenylglycine, 2,4-difluorophenylglycine, 2,5-difluorophenylglycine, 2,6-difluorophenylglycine, 3,4-difluorophenylglycine, 3,5-difluorophenylglycine, 2-(trifluoromethyl)phenylglycine, 3-(trifluoromethyl)phenylglycine, 4-(trifluoromethyl)phenylglycine, 2-(2-thienyl)glycine, 2-(3-thienyl)glycine, 2-(2-furyl)glycine, 3-pyridylglycine, 4-fluorophenylalanine, 4-chlorophenylalanine, 2-bromophenylalanine, 3-bromophenylalanine, 4-bromophenylalanine, 2-naphthylalanine, 3-(2-quinoyl)alanine, 3-(9-anthracenyl)alanine, 2-amino-3-phenylbutanoic acid, 3-chlorophenylalanine, 3-(2-thienyl)alanine, 3-(3-thienyl)alanine, 3-phenylserine, 3-(2-pyridyl)serine, 3-(3-pyridyl)serine, 3-(4-pyridyl)serine, 3-(2-thienyl)serine, 3-(2-furyl)serine, 3-(2-thiazolyl)alanine, 3-(4-thiazolyl)alanine, 3-(1,2,4-triazol-1-yl)-alanine, 3-(1,2,4-triazol-3-yl)-alanine, hexafluorovaline, 4,4,4-trifluorovaline, 3-fluorovaline, 5,5,5-trifluoroleucine, 2-amino-4,4,4-trifluorobutyric acid, 3-chloroalanine, 3-fluoroalanine, 2-amino-3-fluorobutyric acid, 3-fluoronorleucine, 4,4,4-trifluorothreonine, L-allylglycine, tert-Leucine, propargylglycine, vinylglycine, S-methylcysteine, cyclopentylglycine, cyclohexylglycine, 3-hydroxynorvaline, 4-azaleucine, 3-hydroxyleucine, 2-amino-3-hydroxy-3-methylbutanoic acid, 4-thiaisoleucine, acivicin, ibotenic acid, quisqalic acid, 2-indanylglycine, 2-aminoisobutyric acid, 2-cyclobutyl-2-phenylglycine, 2-isopropyl-2-phenylglycine, 2-methylvaline, 2,2-diphenylglycine, 1-amino-1-cyclopropanecarboxylic acid, 1-amino-1-cyclopentanecarboxylic acid, 1-amino-1-cyclohexanecarboxylic acid, 3-amino-4,4,4-trifluorobutyric acid, 3-phenylisoserine, 3-amino-2-hydroxy-5-methylhexanoic acid, 3-amino-2-hydroxy-4-phenylbutyric acid, 3-amino-3-(4-bromophenyl)propionic acid, 3-amino-3-(4-chlorophenyl)propionic acid, 3-amino-3-(4-methoxyphenyl)propionic acid, 3-amino-3-(4-fluorophenyl)propionic acid, 3-amino-3-(2-fluorophenyl)propionic acid, 3-amino-3-(4-nitrophenyl)propionic acid, and 3-amino-3-(1-naphthyl)propionic acid. These non-natural amino acids are commercial available from the following commercial suppliers including Aldrich, Sigma, Fluka, Lancaster, ICN, TCI, Advanced ChemTech, Oakwood Products, Indofine Chemical Company, NSC Technology, PCR Research Chemicals, Bachem, Acros Organics, Celgene, Bionet Research, Tyger Scientific, Tocris, Research Plus, Ash Stevens, Kanto, Chiroscience, and Peninsula Lab. The following amino acids can be synthesized according to literature procedures: 3,3,3-trifluoroalanine (Sakai, T.; et al. Tetrahedron 1996, 52, 233) and 3,3-difluoroalanine (D'Orchymont, H. Synthesis 1993, 10, 961). When A is an amino acid, preferred amino acid for compound of formula I is Leu, Val, Ile, Ala, Pro, Phe, Trp, Met, Tyr. Preferred amino acid for compound of formula II and III is Arg and Lys. When A is a basic amino acid such as glutamine, it may be present as the corresponding amide, alkylamide and dialkyl amide.

With respect to $R_1$ and $R_3$, preferred alkyl groups are $C_{1-6}$ alkyl groups, e.g. methyl, ethyl, propyl, isopropyl, isobutyl, pentyl and hexyl groups. One of the most preferred $R_1$ and $R_3$ groups is methyl. Another of the most preferred $R_1$ and $R_3$ groups is that $R_1$ is hydrogen and $R_3$ is an alkyl group.

With respect to $R_2$, preferred $R_2$ are alkyl groups substituted by an electronegative group or leaving group, including fluoromethyl, chloromethyl, alkoxymethyl, aryloxymethyl, heteroaryloxymethyl, alkylthiomethyl, arylthiomethyl, arylalkylthiomethyl, aminomethyl, acyloxymethyl, and arylacyloxymethyl. Other examples of optional substituents that may be present at the $R_2$ alkyl group include, without limitation, 3-pyrazolyloxy optionally substituted at the 2, 4 and 5-positions with lower alkyl; 3-(1-phenyl-3-trifluoromethyl)pyrazolyloxy (PTP); 2,6-di(trifluoromethyl)benzoyloxy; 2,6-dimethylbenzoyloxy, pentafluoro-phenoxy; 2,6-dichlorobenzoyloxy (DCB); 2-(3-(2-imidazolyl)naphthyl)oxy; diphenylphosphinyloxy; tetronyloxy; and tetramoyloxy. Modification with DCB or PTP can be made according to the techniques disclosed in U.S. Pat. No. 6,495,522; Dolle, R. E. et al., *J. Med. Chem.* 37: 563-4 (1994); or Dolle, R. E. et al., *J. Med. Chem.* 37: 3863-6 (1994); all of which are wholly incorporated by reference herein.

With respect to $R_4$, preferred alkyl are methyl, ethyl, isopropyl, isobutyl; preferred substituents on alkyl are hydroxy, carboxy, halogen, $C_4$-$C_7$ cycloalkyl, saturated and unsaturated heterocyclic, aryl or heteroaryl; preferred cycloalkyl are cyclopentyl and cyclohexyl; preferred saturated and unsaturated heterocyclic groups are piperidinyl and morpholinyl; preferred aryls are phenyl and naphthyl; preferred heteroaryls are pyridyl, indolyl, furyl and thienyl; preferred substituents on the aryl and heteroaryl are methyl, ethyl, chloro, fluoro, bromo, trifluoromethyl, methoxy, hydroxy, carboxy, cyano and nitro. Preferred heterocylic include cycloamines such as piperazine, piperidine, morpholine and N-methylpiperazine.

With respect to $R_6$ and $R_7$, preferably one of the $R_6$ and $R_7$ is a hydrogen. With respect to $R_8$ and $R_9$, preferably one of the $R_8$ and $R_9$ is hydrogen, or preferably both $R_8$ and $R_9$ are hydrogen. Preferably n is 1.

The compounds represented by Formula I-X are inhibitors of proteases of SARS-CoV and coronaviruses and block the protease of SARS-CoV and coronaviruses, and the replication of these viruses. Therefore, the invention is also related to methods of treating, preventing or ameliorating conditions in which SARS-CoV and coronaviruses plays a role. These conditions are more fully described below.

The compounds represented by Formula I-X also are inhibitors of proteases of picornaviruses and block the replication of these viruses, including poliovirus and coxsackievirus (Enterovirus), foot-and mouth disease virus (Aphthovirus), encephalomyocarditis virus (Cardiovirus), hepatitis A virus (Hepatovirus), and human rhinoviruses (Rhinovirus). Therefore, the invention is also related to methods of treating, preventing or ameliorating conditions in which picornaviruses plays a role.

The methods comprise administering to an animal in need of such treatment an inhibitor of the present invention, or a pharmaceutically acceptable salt or prodrug thereof, in an amount effective to inhibit SARS-CoV and coronaviruses, or picornaviruses.

Exemplary preferred inhibitors of protease of SARS-CoV and coronaviruses, or picornaviruses having Formulae I-X include, without limitation:

Cbz-Leu-Gln-fmk;
4-(Cbz-Val-Leu-amido)-6-fluoro-5-oxo-hexanoic acid dimethylamide;
4-(Cbz-Leu-amido)-6-Fluoro-5-oxo-hexanoic acid methylamide;
(This is same as Cbz-Leu-Gln-fmk)
4-(Cbz-Ile-amido)-6-fluoro-5-oxo-hexanoic acid methylamide;
4-(Cbz-Val-amido)-6-fluoro-5-oxo-hexanoic acid methylamide;
3-(Cbz-Val-amido)-5-fluoro-4-oxo-pentanoic acid dimethylamide;
(This is Z-VD-fmk)
4-(Cbz-Leu-amido)-6-Fluoro-5-oxo-hexanoic acid dimethylamide;
4-(Cbz-Ile-amido)-6-Fluoro-5-oxo-hexanoic acid dimethylamide;
4-(Cbz-Val-amido)-6-Fluoro-5-oxo-hexanoic acid dimethylamide;
4-(Cbz-Ala-amido)-6-Fluoro-5-oxo-hexanoic acid dimethylamide;
4-(Cbz-Gly-amido)-6-Fluoro-5-oxo-hexanoic acid dimethylamide;
Ac-Leu-Gln-fmk;
Cbz-Val-Gln-fmk;
Ac-Val-Gln-fmk;
Cbz-Ile-Gln-fmk;
Ac-Ile-Gln-fmk;
Cbz-Leu-Gln-DCB-methylketone;
Cbz-Gln-fmk;
Ac-Gln-fmk;
Cbz-Arg-Gly-fmk;
Ac-Arg-Gly-fmk;
Cbz-Lys-Gly-fmk;
Ac-Lys-Gly-fmk;
Cbz-Arg-Gly-DCB-methylketone;
Cbz-Gly-fmk;
Ac-Gly-fmk;
Cbz-Arg-Ala-fmk;
Ac-Arg-Ala-fmk;
Cbz-Lys-Ala-fmk;
Ac-Lys-Ala-fmk;
Cbz-Arg-Ala-DCB-methylketone;

Cbz-Ala-fmk;
Ac-Ala-fmk;

where Cbz is benzyloxycarbonyl, DCB is 2,6-dichlorobenzoyloxy and fmk is fluoromethylketone.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups include straight chained and branched $C_{2-10}$ alkenyl groups, more preferably $C_{2-6}$ alkenyl groups. Typical $C_{2-10}$ alkenyl groups include ethenyl, propenyl, isopropenyl, butenyl, pentenyl, hexenyl and octenyl groups.

Useful alkynyl groups include straight chained and branched $C_{2-10}$ alkynyl groups, more preferably $C_{2-6}$ alkynyl groups. Typical $C_{2-10}$ alkynyl groups include ethynyl, propynyl, butynyl, pentynyl, hexynyl and octynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above. Also included are the sulfoxides and sulfones of such alkylthio groups.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g. 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Protecting groups $R_5$ include, without limitation, the groups having Formulae IVa, IVb and IVc. Particular examples include alkanoyl (e.g. acetyl, proponoyl, t-butanoyl), benzyloxycarbonyl, and t-butoxycarbonyl.

Optional substituents include one or more alkyl; halo; haloalkyl; cycloalkyl; aryl optionally substituted with one or more lower alkyl, halo, haloalkyl or heteroaryl groups; aryloxy optionally substituted with one or more lower alkyl, halo, haloalkyl or heteroaryl groups; aralkyl; heteroaryl optionally substituted with one or more lower alkyl, haloalkyl and aryl groups; heteroaryloxy optionally substituted with one or more lower alkyl, haloalkyl and aryl groups; alkoxy; alkylthio; arylthio; amino; acyloxy; arylacyloxy optionally substituted with one or more lower alkyl, halo alkyl and aryl groups; diphenylphosphinyloxy optionally substituted with one or more lower alkyl, halo or haloalkyl groups; heterocyclo optionally substituted with one or more lower alkyl, haloalkyl and aryl groups; heterocycloalkyloxy optionally substituted with one or more lower alkyl, haloalkyl and aryl groups; partially unsaturated heterocycloalkyl optionally substituted with one or more lower alkyl, haloalkyl and aryl groups; or partially unsaturated heterocycloalkyloxy optionally substituted with one or more lower alkyl, haloalkyl and aryl groups.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy and Tris(hydroxymethyl)aminomethane (TRIS, tromethane).

Examples of prodrugs include compounds of Formulae I-X wherein $R_1$ is an alkyl group or substituted alkyl group such as $CH_2OCH_3$ and $CH_2OCOCH_3$ (AM ester).

The compounds of this invention may be prepared using methods known to those skilled in the art, or the novel method of this invention. The protease inhibitors of formula I can be prepared as exemplified in Scheme 1. The ester 1 can be converted to the amide 2 by reaction with ammonia, such as in ammonia/methanol. Reaction of amide 2 with the aldehyde intermediate which is produced by Swern-oxidation of 2-fluoroethanol will produce the nitro-alcohol 3. Reduction of 3 by hydrogenation will produce the amino-alcohol 4. Coupling of 4 with a N-protected leucine such as Z-Leu-OH will give amide 5, which can be oxidized by Dess-Martin reagent or PCC (pyridinium chlorochromate) to produce 6. For the preparation of compounds with alkyl groups on the amide group of glutamine, a substituted amine was used instead of ammonia to prepare 2. For example, reaction of 1 with methylamine produced the methylamide analog, and reaction of 1 with dimethylamine produced the dimethylamide analog.

The protease inhibitors of formula II can be prepared as exemplified in Scheme 2. Reaction of nitroethane 7 with the aldehyde intermediate will produce the nitro-alcohol 8. Reduction of 8 by hydrogenation will produce the amino-alcohol 9. Coupling of 9 with a N-protected arginine such as Z-Arg-OH will give amide 10, which can be oxidized by Dess-Martin reagent to produce 11.

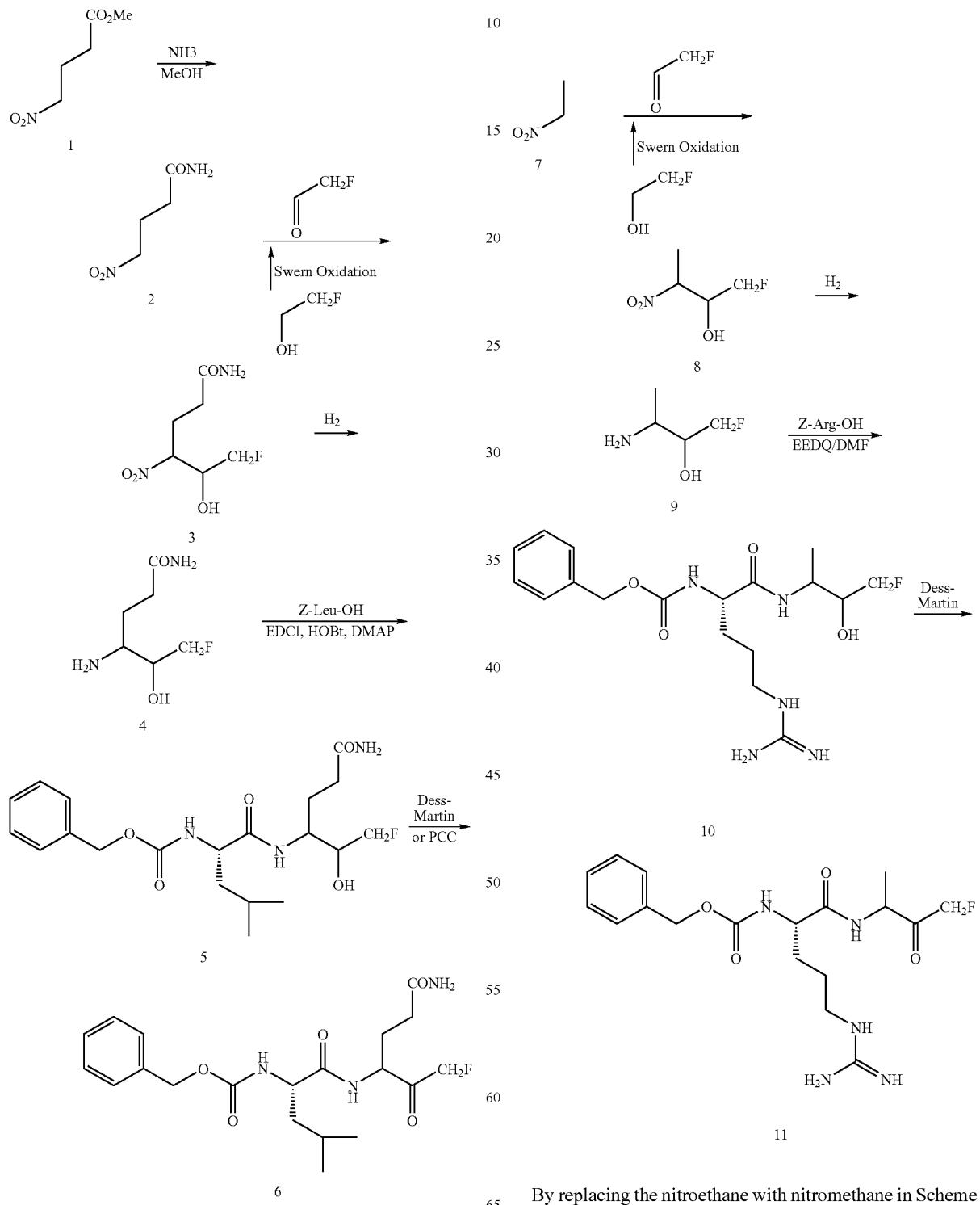

By replacing the nitroethane with nitromethane in Scheme 2, the reaction will produce the protease inhibitors of formula III as exemplified in Scheme 3.

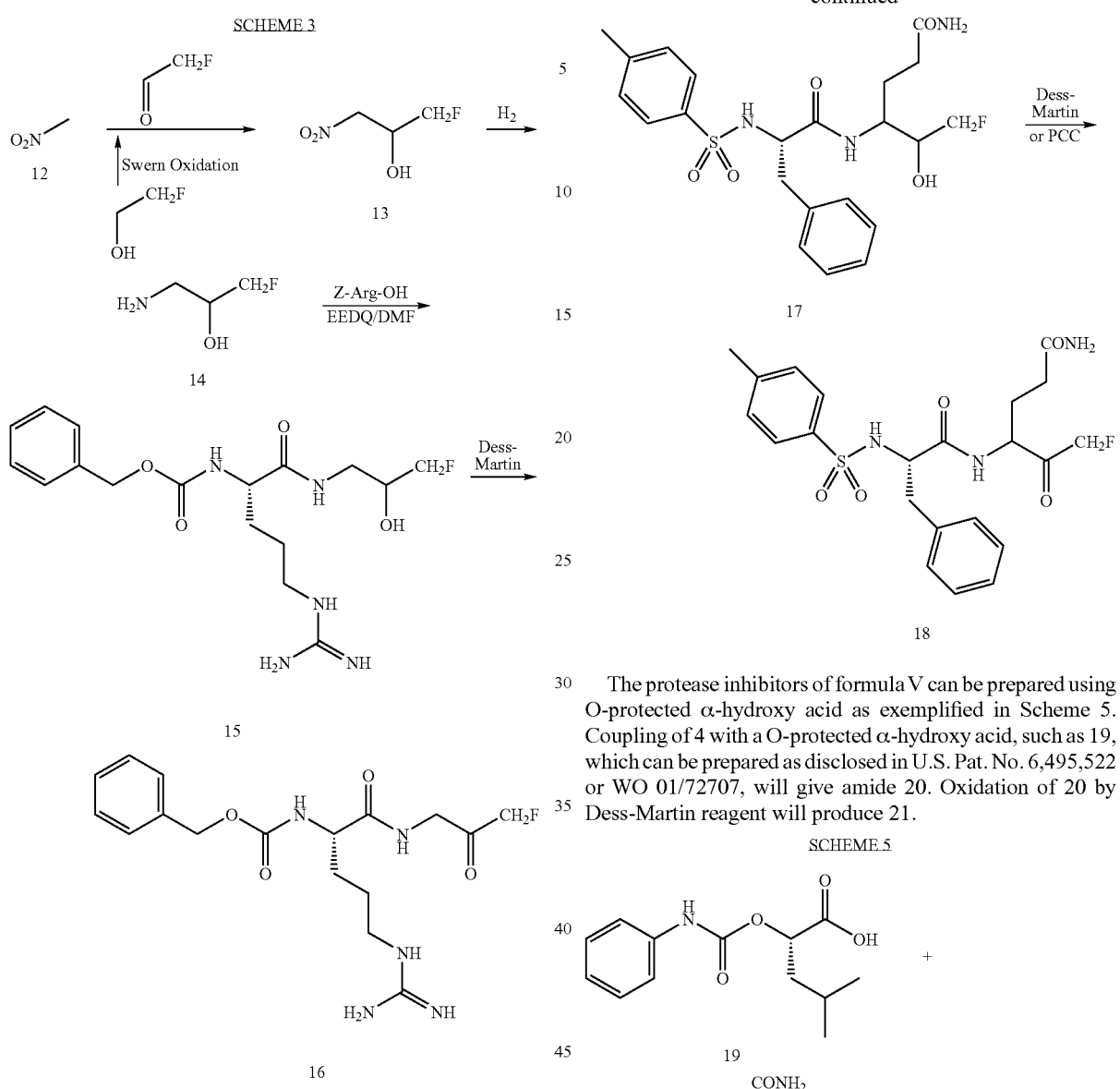

The protease inhibitors of formula IV can be prepared using N-protected amino acid or peptide as exemplified in Scheme 4. Coupling of 4 with a N-protected amino acid, such as TOS-Phe-OH will give amide 17, which can be oxidized by Dess-Martin reagent to produce 18.

The protease inhibitors of formula V can be prepared using O-protected α-hydroxy acid as exemplified in Scheme 5. Coupling of 4 with a O-protected α-hydroxy acid, such as 19, which can be prepared as disclosed in U.S. Pat. No. 6,495,522 or WO 01/72707, will give amide 20. Oxidation of 20 by Dess-Martin reagent will produce 21.

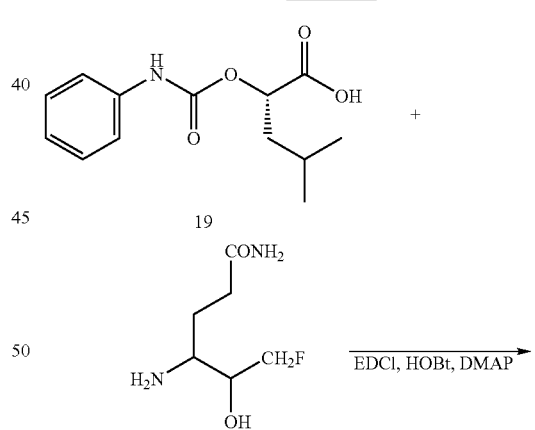

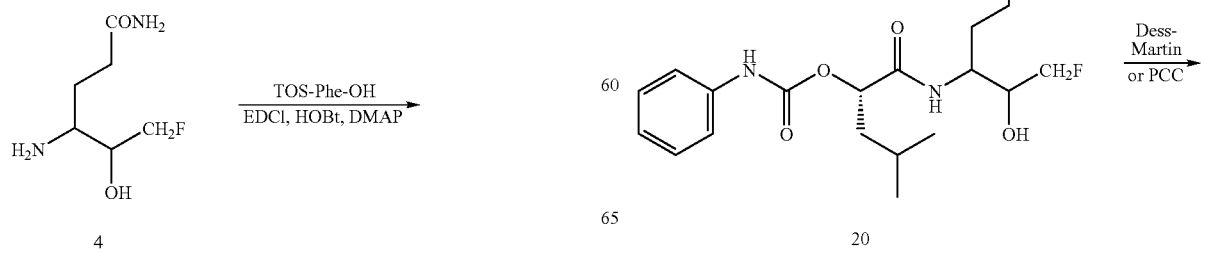

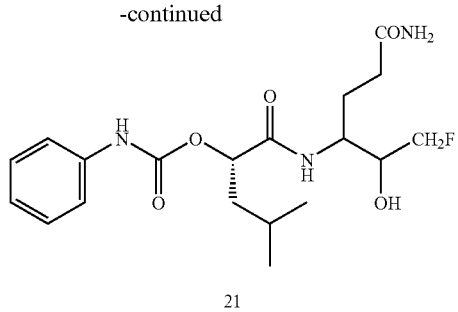

21

The protease inhibitors of formula VI can be prepared using substituted succinic acid as exemplified in Scheme 6. Coupling of 4 with a substituted succinic acid, such as 22 will give amide 23. Oxidation of 23 by Dess-Martin reagent will produce 24. The ethyl ester group can be converted to other groups, such as by hydrolysis under basic conditions followed by a coupling reaction with an amine.

SCHEME 6

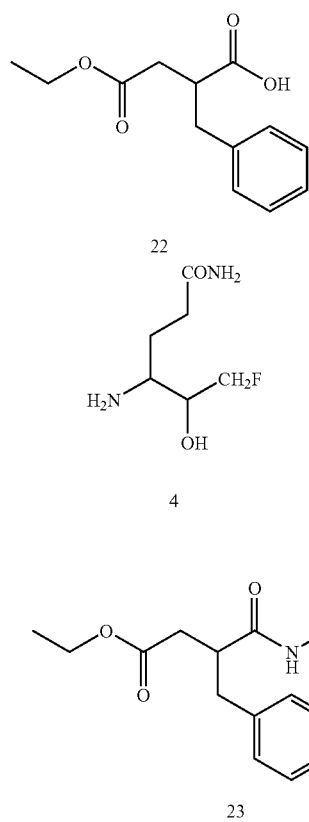

The protease inhibitors of formula VII can be prepared using substituted pyridone as exemplified in Scheme 7. Coupling of 4 with a substituted pyridone, such as 25, which can be prepared following reported procedure (Semple et al., *Bioorg. Med. Chem. Lett.* 7, 1337-1342, 1997), will give amide 26. Oxidation of 26 by Dess-Martin reagent will produce 27.

SCHEME 7

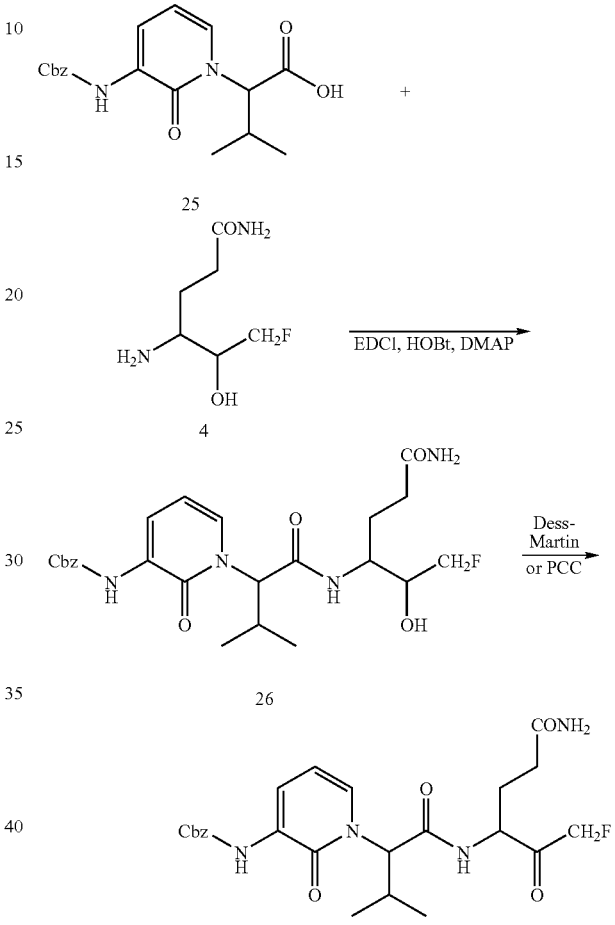

The protease inhibitors of formula VIII can be prepared using substituted pyridone as exemplified in Scheme 8. Reaction of substituted pyridone, such as 28 with a substituted 2-bromoacetate, such as 29 following a reported procedure (Semple et al., *Bioorg. Med. Chem. Lett.* 7, 1337-1342, 1997), will give the pyridone-substituted ester 30, which can be hydrolyzed by a base, such as NaOH, to produce the acid 31. Coupling of 31 with amine 4 will give amide 32. Oxidation of 32 by Dess-Martin reagent will produce 33.

SCHEME 8

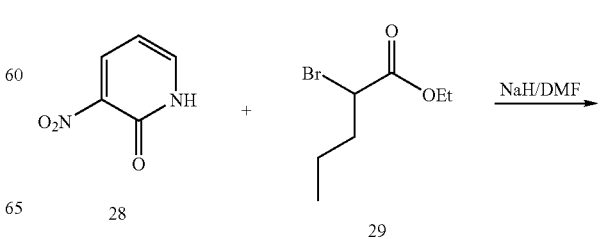

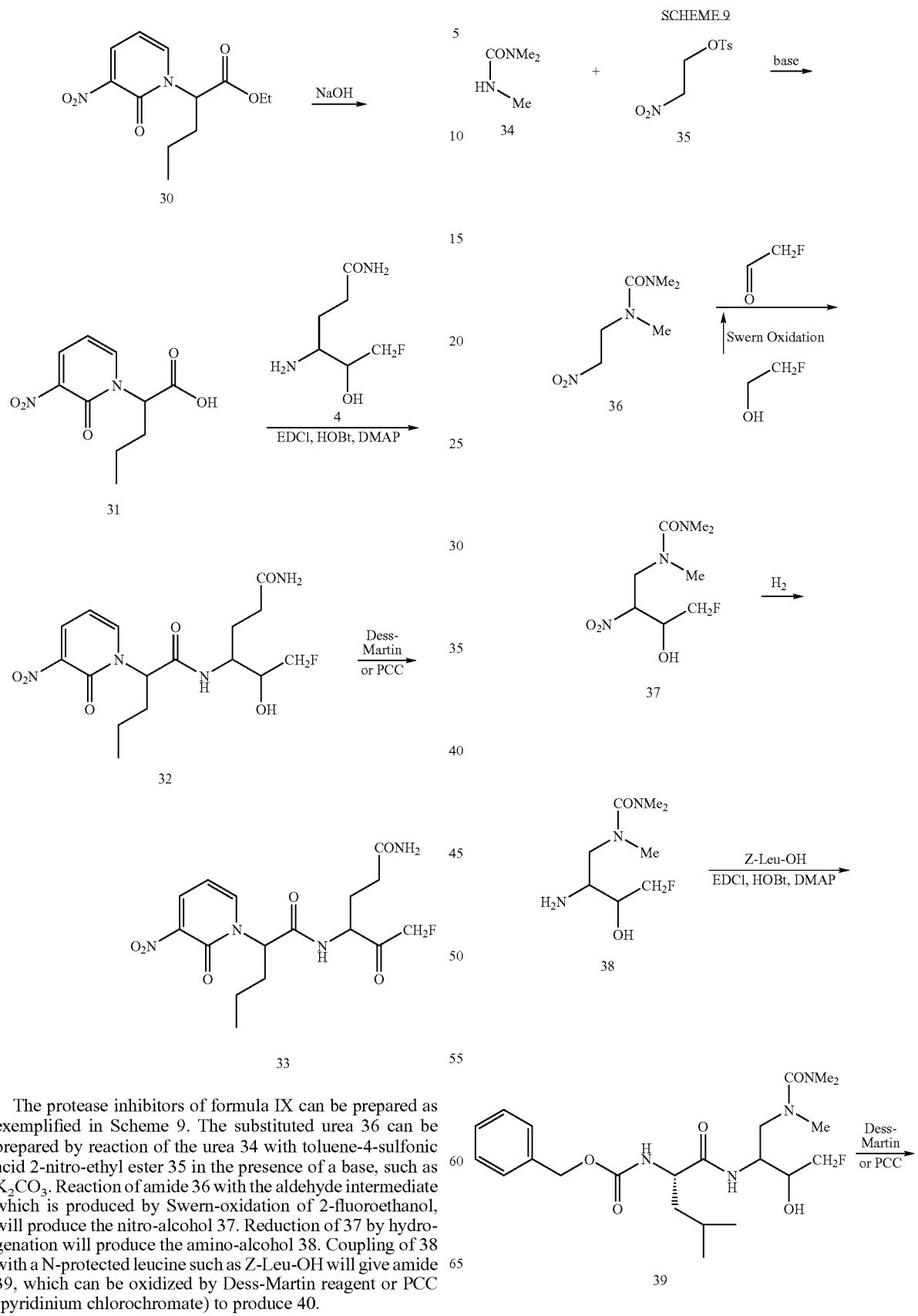

The protease inhibitors of formula IX can be prepared as exemplified in Scheme 9. The substituted urea 36 can be prepared by reaction of the urea 34 with toluene-4-sulfonic acid 2-nitro-ethyl ester 35 in the presence of a base, such as $K_2CO_3$. Reaction of amide 36 with the aldehyde intermediate which is produced by Swern-oxidation of 2-fluoroethanol, will produce the nitro-alcohol 37. Reduction of 37 by hydrogenation will produce the amino-alcohol 38. Coupling of 38 with a N-protected leucine such as Z-Leu-OH will give amide 39, which can be oxidized by Dess-Martin reagent or PCC (pyridinium chlorochromate) to produce 40.

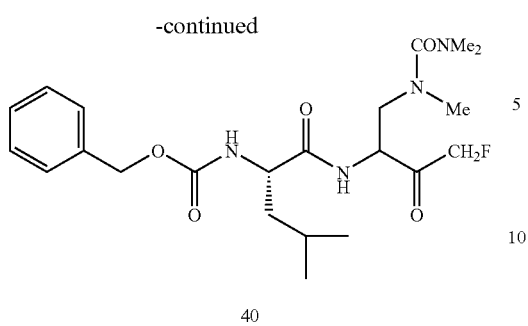

40

The protease inhibitors of formula XI, wherein $R_{16}$ and one of the $R_1$ or $R_3$, together with the attached atoms formed a heterocycle, can be prepared as exemplified in Scheme 10. The substituted cyclized urea 42 can be prepared by reaction of the urea 41 with toluene-4-sulfonic acid 2-nitro-ethyl ester 35 in the presence of a base, such as NaH. The final product 43 can be prepared similar to Scheme 9 started from 42 in four steps.

SCHEME 10

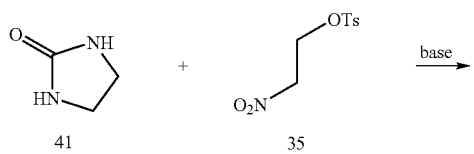

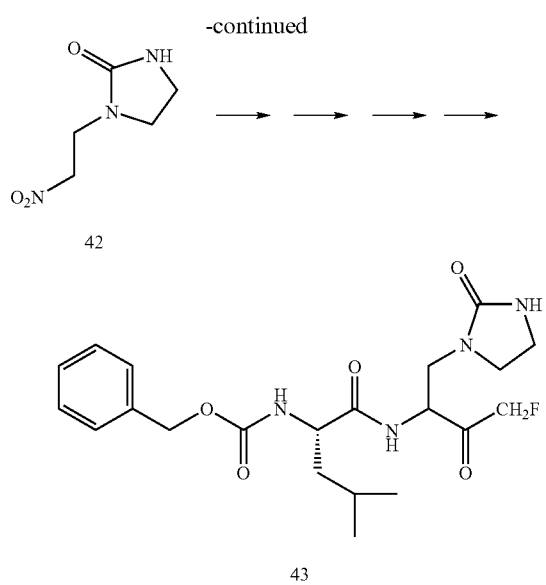

The protease inhibitors of formula VI also can be prepared using substituted succinic acid as exemplified in Scheme 11. Coupling of acid 44 with a substituted amine, such as benzylamine, followed by hydrolysis should produce acid 45. Coupling of 45 with the amine intermediate followed by oxidation similar to Scheme 6 will produce the product 46.

SCHEME 11

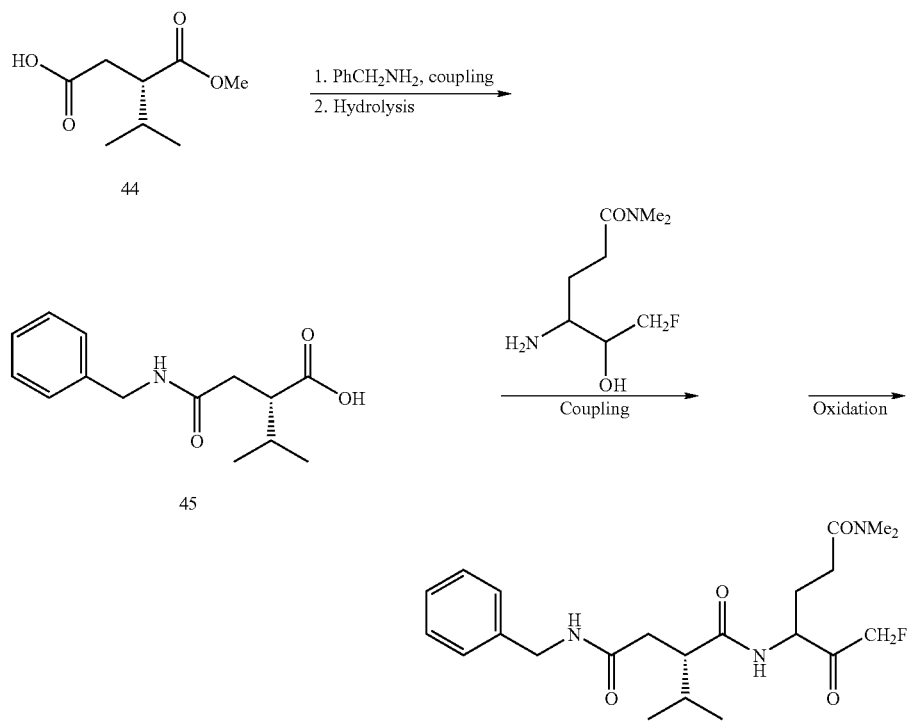

The protease inhibitors of formula IV, wherein $R_2$ is a substituted alkyl $CH_2X$ and X is dichlorobenzoyloxy, can be prepared as exemplified in Scheme 12. Coupling of acid 47 with the amine, followed by deprotection of the t-Bu group should produce the acid 48. Treatment of the acid 48 with EtOCOCl, then with diazomethane will convert it into the diazomethylketone, followed by treatment with HBr to produce the bromomethylketone 49. Reaction of the bromomethylketone 49 with 2,6-dichlorobenzoic acid will produce the DCB compound 50. Deprotection of the Cbz group by hydrogenation provides the amine 51, which will be used to couple with a Cbz protected acid such as Cbz-Val to give the product 52.

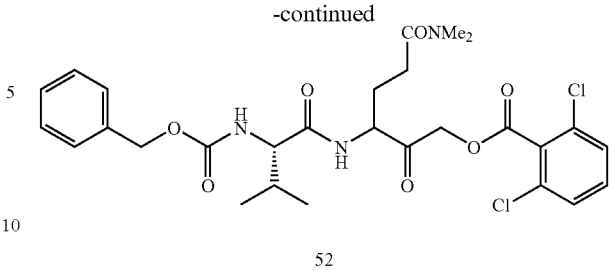

52

The protease inhibitors of formula IV, wherein the Gln portion is prepared starting from a chiral starting material and prepared as a single stereoisomer, can be prepared as exemplified in Scheme 13. Starting from Boc-L-Gln(N,N-Me$_2$), the chiral intermediate 58 will be prepared according to published procedures (Morris, T. S. et al. *Bioorg. Med. Chem.* 1997, 5: 97-807), which will be used for the coupling with a Cbz protected acid such as Cbz-Val to give the product 59 as a single stereoisomer.

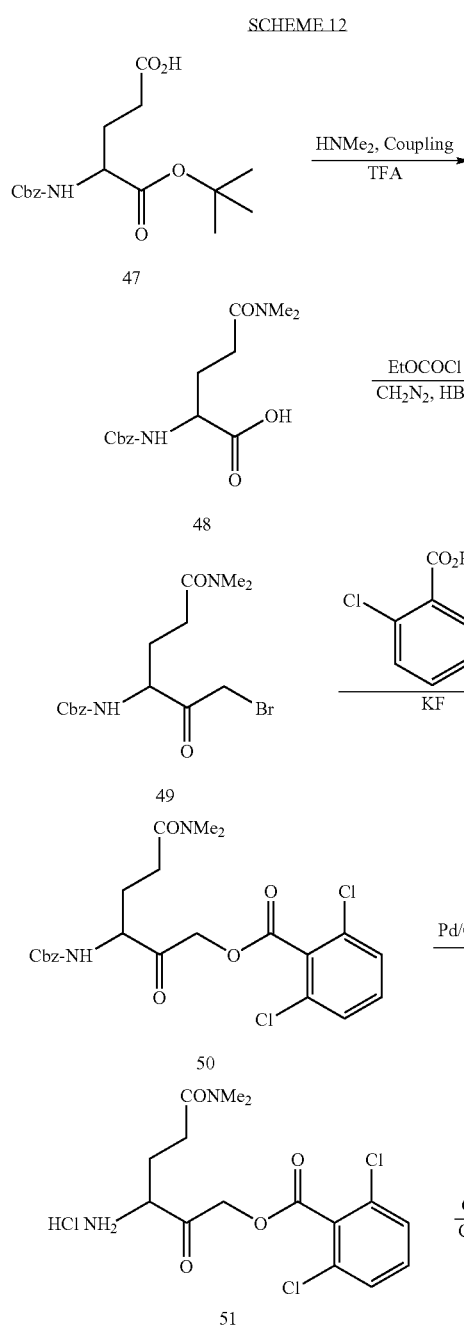

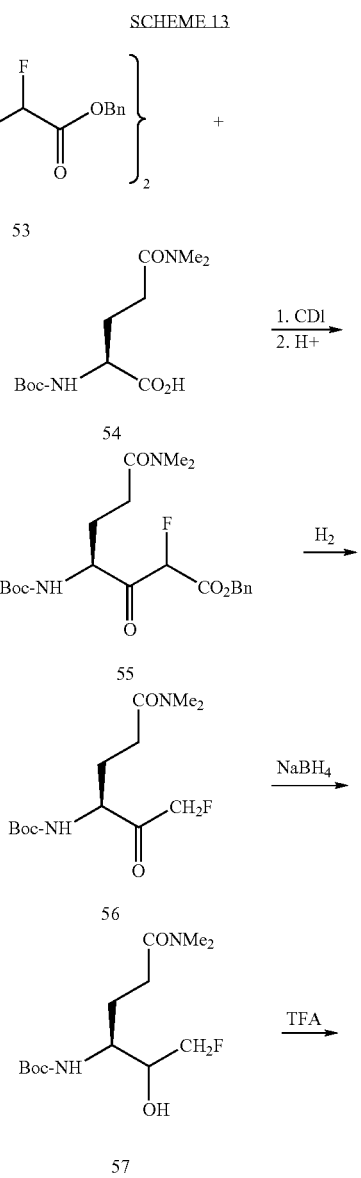

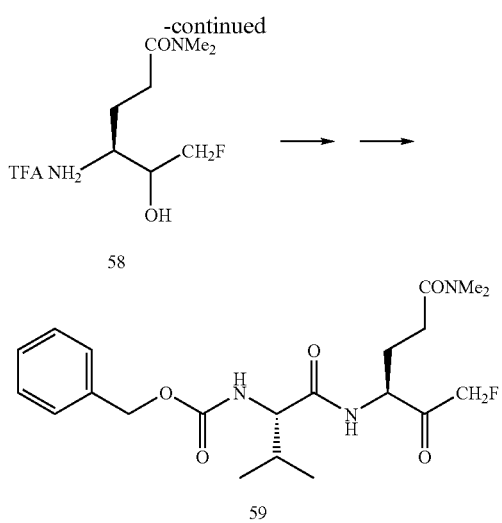

-continued

58

59

These compounds can be tested for protease inhibiting activity by several methods. For example, these compounds can be tested for protease inhibiting activity using known coronavirus proteases, such as FIPV 3CL$^{pro}$ (Hegyi A. and Ziebuhr J. J. Gen. Virol. 2002, 83:595-9; and Hegyi, A. et al. J. Gen. Virol. 2002, 83:581-593), or SARS-CoV M$^{pro}$ (Yang et al, Proc. Natl. Acad. Sci. USA, 2003, 100: 13190-13195). These compounds also can be tested for protease inhibiting activity using coronavirus infected cells, such as MHV-A59 infected murine DBT cells (Kim, J. C. et al. Virology, 1995, 208:1-8), or SARS-CoV infected Vero-cells (Drosten, C. et al. N. Engl. J. Med. 2003, 348: 1967-76). The SARS-CoV infected Vero-cells assays measure the protective effects of compounds against SARS-CoV-induced cell death (cytopathic effect (CPE)), as a measurement of the inhibiting effects of compounds on the replication of SARS-CoV (Cinatl J, et al. Lancet, 2003, 361: 2045-6; and Tan E. L. C. et al. Emerg. Infect. Dis. 2004, 10: 581-586).

An important aspect of the present invention is that compounds having Formulae I-X are inhibitors of protease of SARS-CoV and coronaviruses. Therefore, these inhibitors are expected to block or kill the SARS-CoV and coronaviruses in a variety of clinical conditions in which there is an infection of SARS-CoV and coronaviruses, including animals and humans.

Another important aspect of the present invention is that compounds having Formulae I-X also are inhibitors of protease of picornaviruses, such poliovirus and coxsackievirus (Enterovirus), foot-and mouth disease virus (Aphthovirus), encephalomyocarditis virus (Cardiovirus), hepatitis A virus (Hepatovirus), and human rhinoviruses (Rhinovirus). Therefore, these inhibitors are expected to block or kill the picornaviruses in a variety of clinical conditions in which there is an infection of picornaviruses, including animals and humans.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for SARS-CoV or coronaviruses mediated disorders. Preferably, about 0.01 to about 10 mg/kg is orally administered to treat or prevent such disorders. For intramuscular injection, the dose is generally about one-half of the oral dose. The drugs also can be administered by IV, inhalation, nose spray.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular compounds of the present invention with a solution of a pharmaceutically acceptable non-toxic base such as sodium hydroxide, potassium hydroxide, choline hydroxide, sodium carbonate Tris and the like.

The pharmaceutical compositions of the invention may be administered to any animal which may experience the beneficial effects of the compounds of the invention. Foremost among such animals are mammals, e.g., humans and veterinary animals such as cows, sheep, horses, chickens and the like, although the invention is not intended to be so limited.

The inhibitors of protease of SARS-CoV and coronaviruses, and picornaviruses, such as poliovirus and coxsackievirus (Enterovirus), foot-and mouth disease virus (Aphthovirus), encephalomyocarditis virus (Cardiovirus), hepatitis A virus (Hepatovirus), and human rhinoviruses (Rhinovirus), and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, inhalation or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, antiviral agents and carriers, etc., that are known or apparent to those skilled in the art. The compositions of the invention are administered to an animal in need thereof, e.g. an animal already suffering from coronavirus infection, suspected of having coronavirus infection or at risk of acquiring coronavirus infection. When one administers the compound to an animal at risk of coronavirus infection, the intention is to try to avoid coronavirus infection of the animal, e.g. by preventing the spread of the virus to the animal from another source.

The invention also provides methods for preventing or reducing the spread of coronavirus or picornavirus, comprising contacting an article or waste suspected of being contaminated with a coronovirus with a compound of the present invention. Typically, the compound is present in solution, e.g. in water optionally with a detergent or non-ionic surfactant. In this embodiment, the surface of the article is contacted with a solution comprising the compound. Examples of such articles include without limitation medical instruments such as forceps, intabation tubes, and scalpels; bandages and face masks; examination tables and other furniture; floors and the like. In another embodiment, infectious waste from a patient infected with coronavirus is treated with a compound according to the present invention. Such infectious waste includes, without limitation, sputum, blood, urine, cerebrospinal fluid, and feces.

The invention further provides method for preventing the replication of coronavirus, or picornavirus, comprising contacting the coronavirus with a compound of the present invention. Such coronavirus may contaminate an article or infectious waste as described above, or present in a cell, tissue or animal as an infectious organism.

EXAMPLE 1

4-Nitro-Butyramide

To a solution of methyl 4-nitrobutyrate (8.83 g, 60 mmol) in methanol (20 mL) at 0° C. was added a solution of ammonia in methanol (7N, 30 mL). The solution was then warmed to room temperature and stirred at for 72 h. The solvent was evaporated and the residue was re-crystallized from ethyl acetate to give the title product (6.2 g, 78%). $^1$H NMR (acetone-d$_6$): 6.86 (bs, NH, 1H), 6.28 (bs, NH, 1H), 4.59 (t, J=6.9 Hz, 2H), 2.36-2.30 (m, 2H), 2.28-2.20 (m, 2H).

EXAMPLE 2

6-Fluoro-5-Hydroxy-4-Nitro-Hexanoic Acid Amide

To a solution of oxalyl chloride (5.29 g, 41.4 mmol) in anhydrous dichloromethane (30 mL) at −78° C. was added anhydrous DMSO (6.2 mL, 87.4 mmol) dropwise with stirring in such a rate that the temperature was kept at −50 to −60° C. The solution was stirred for 15 min, then 2-fluoroethanol (1.62 mL, 27.6 mmol) was added dropwise and it was stirred for 15 min, diluted with dichloromethane (100 mL), followed by addition of dry Et$_3$N (13.5 mL). The reaction mixture was stirred for 15 min, then allowed to warm to 0° C. and stirred at 0° C. for 2 h. To the reaction mixture was added a solution of 4-nitro-butyramide (3.04 g, 23 mmol) in CH$_2$Cl$_2$/THF (50 mL, 1:1). The reaction mixture was stirred at 0° C. for 3 h and then stirred at room temperature overnight. The mixture was concentrated to approximate 20 mL and poured into water (180 mL). It was extracted with ethyl acetate (12×40 mL), and the combined organic layers were dried and evaporated and the residue was purified by silica gel (CH$_2$Cl$_2$/EtOAc) to give 1.84 g (41%) of the titled product as a colorless viscous oil. $^1$H NMR (acetone-d$_6$): 6.88 (bs, NH, 1H), 6.31 (bs, NH, 1H), 5.20-4.20 (m, 5H), 2.40-2.15 (m, 4H).

EXAMPLE 3

4-Amino-6-Fluoro-5-Hydroxy-Hexanoic Acid Amide

To a solution of 6-fluoro-5-hydroxy-4-nitro-hexanoic acid amide (0.5 g, 2.58 mmol) in MeOH (20 mL) was added Raney Ni (about 200 mg), and the mixture was shaken under H$_2$ (40-45 psi) at room temperature for 6 h. It was filtered and the catalyst was washed with MeOH (3×10 mL). The MeOH solution was evaporated and the residue oil (435 mg) was used without further purification. $^1$H NMR (acetone-d$_6$): 6.85 (bs, NH, 1H), 6.15 (bs, NH, 1H), 4.70-4.25 (m, 3H), 3.65-3.50 (m, 1H), 2.86 (bs, 2H), 2.40-2.20 (m, 4H).

EXAMPLE 4

4-(Cbz-Leu-Amido)-6-Fluoro-5-Hydroxy-Hexanoic Acid Amide

To a solution of Cbz-Leucine (132.7 mg, 0.5 mmol) in THF (20 mL) was added EDCI (96 mg, 0.5 mmol), HOBT (67.5 mg, 0.5 mmol) and DMAP (130.5 mg 0.25 mmol). The resulting mixture was stirred for 10 min, then was added a solution of 4-amino-6-fluoro-5-hydroxy-hexanoic acid amide (82 mg, 0.5 mmol) in DMF (2 mL), and it was stirred at room temperature overnight. The solvent was evaporated and the residue was diluted with ethyl acetate (20 mL). The solution was washed with water (4×20 mL), and the organic layer was dried and evaporated. The residue was purified by chromatography over silica gel (hexane-EtOAc, 1:1 to EtOAc/MeOH=3:1) to give 85 mg (41%) of the titled compound as a white solid. $^1$H NMR (acetone-d$_6$): 7.38-7.15 (m, 5H), 7.08 (bs, 1H), 6.80 (bs, 1H), 6.54 (bs, 1H), 6.31 (bs, 1H), 5.09 (s, 2H), 4.70-3.80 (m, 5H), 2.20 (t, J=6.90 Hz, 1H), 1.85 (m, 2H), 1.75 (m, 1H), 1.62 (m, 2H), 0.93 (m, 6H).

EXAMPLE 5

Cbz-Leu-Gln-Fmk

To a solution of 4-(CBz-Leu-amido)-6-fluoro-5-hydroxyhexanoic acid amide (82 mg, 0.2 mmol) in CH$_2$Cl$_2$ (20 mL) at 0° C. was added Dess-Martin periodinane (254 mg, 0.6 mmol) in CH$_2$Cl$_2$ (12 mL), and the resulting white mixture was stirred at room temperature for 4 h. The solvent was evaporated and the residue was diluted with ethyl acetate (40 mL). It was washed with water (5×20 mL), and the organic layer was dried and concentrated. The residue was purified by column chromatography (EtOAc/MeOH 8:1) to give the title product (18 mg, 22%) as a mixture of cyclized form and open form based on $^1$H NMR. $^1$H NMR (acetone-d$_6$): 7.38-7.15 (m, 5H), 7.10-7.00 (m, 1.2H), 6.60 (m, 1H), 6.31 (bs, 0.2H), 5.09 (s, 2H), 4.55-4.15 (m, 4H), 2.35 (m, 2H), 1.76 (m, 2H), 1.65 (m, 2H), 0.93 (m, 6H).

EXAMPLE 6

4-(Cbz-Val-Leu-Amido)-6-Fluoro-5-Hydroxy-Hexanoic Acid Dimethylamide

The title compound was prepared similar to Example 4. From Cbz-Val-Leu (189.9 mg, 0.521 mmol) and of 4-amino-6-fluoro-5-hydroxy-hexanoic acid dimethylamide (100 mg, 0.521 mmol) was obtained 56 mg (20%) of the title compound. $^1$H NMR (acetone-d$_6$): 7.70-7.05 (m, 7H), 6.60-6.40 (m, 1H), 5.20-5.00 (m, 2H), 5.60-3.70 (m, 6H), 6.80 (bs, 1H), 2.90-2.70 (m, 6H), 2.45-2.30 (m, 2H), 2.15 (m, 1H), 1.90 (m, 2H), 1.80-1.50 (m, 4H), 1.05-0.85 (m, 12H).

EXAMPLE 7

4-(Cbz-Val-Leu-Amido)-6-Fluoro-5-Oxo-Hexanoic Acid Dimethylamide

The title compound was prepared similar to Example 5. From 4-(CBz-Val-Leu-amido)-6-fluoro-5-hydroxy-hexanoic acid dimethylamide (26.9 mg, 0.05 mmol) and Dess-Martin reagent (84.9 mg, 0.2 mmol) was obtained 12.8 mg (48%) of the title compound. $^1$H NMR (acetone-d$_6$): 8.00-7.50 (m, 2H), 7.42-7.25 (m, 5H), 6.80-6.50 (m, 1H), 5.40-4.90 (m, 4H), 4.50 (m, 2H), 4.05 (m, 1H), 3.90 (m, 1H), 2.86-2.81 (m, 6H), 2.50-2.35 (m, 2H), 2.24-2.05 (m, 2H), 1.95 (m, 1H), 1.80-1.50 (m, 4H), 1.05-0.85 (m, 12H).

EXAMPLE 8

N-Methyl-4-Nitro-Butyramide

To a sealed reaction vessel was added methyl 4-nitrobutyrate (1.00 g, 6.80 mmol) and methylamine (2.0 M methylamine in MeOH, 50.0 mL, 100 mmol). The resulting yellow solution was stirred at room temperature for 20 h. The solvent was evaporated and the residue was purified by flash chromatography (silica gel, load: CH$_2$Cl$_2$, elution with EtOAc:Hexanes, 1:1) to give the title product (0.97 g, 98%) as a white solid. $^1$H NMR (CDCl$_3$): 5.84 (br s, NH, 1H), 4.54-4.48 (m, 2H), 2.82 (d, J=4.7 Hz, 3H), 2.36-2.32 (m, 4H).

EXAMPLE 9

6-Fluoro-5-Hydroxy-4-Nitro-Hexanoic Acid Methylamide

To a clear solution of oxalyl chloride (2.0 M oxalyl chloride in dichloromethane, 0.868 g, 6.84 mmol) at −74° C. was added anhydrous DMSO (1.06 mL, 14.9 mmol) dropwise over 10 minutes while maintaining the internal temperature <−60° C. The white suspension was stirred for 15 min, then 2-fluoroethanol (0.273 mL, 4.65 mmol) was added dropwise while maintaining the internal temperature <−65° C. The yellow suspension was stirred for 20 minutes and then diluted with dichloromethane (19.5 mL), followed by the addition of anhydrous Et$_3$N (3.90 mL, 28.0 mmol). The reaction mixture was stirred for 15 min at −71° C. and then allowed to warm to 0° C. and stirred at 0° C. for 2 h. To the reaction mixture was added a solution of N-methyl-4-nitro-butyramide (0.570 g, 3.90 mmol) in dichloromethane (2.3 mL). The reaction mixture was stirred at 0° C. for 1 h and then stirred at room temperature overnight. The mixture was concentrated to a white residue, diluted with ethyl acetate (50 mL), and the organic layer was washed with water (25 mL). The aqueous layer was then extracted with ethyl acetate (2×40 mL) and the combined organic layers were dried over MgSO$_4$, concentrated and the residue was purified by flash chromatography (silica gel, gradient elution with EtOAc:Hexanes, 1:1 to 4:1) to give 0.325 g (40%) of the titled product as a colorless viscous oil. $^1$H NMR (CDCl$_3$): 6.88 (br s, NH, 1H), 6.31 (br s, NH, 1H), 5.20-4.20 (m, 5H), 2.40-2.15 (m, 4H).

EXAMPLE 10

4-Amino-6-Fluoro-5-Hydroxy-Hexanoic Acid Methylamide

To a solution of 6-fluoro-5-hydroxy-4-nitro-hexanoic acid methylamide (0.325 g, 1.56 mmol) in MeOH (12 mL) was added Raney Ni (about 0.12 g), and the mixture was shaken under H$_2$ (40-45 psi) at room temperature for 18 h. The black mixture was filtered through celite, and the celite was washed with additional MeOH (100 mL). The yellow solution was concentrated to give yellow oil (0.250 g, 90%), which was used without further purification. $^1$H NMR (CDCl$_3$): 5.68 (br s, NH, 1H), 4.64-4.38 (m, 2H), 3.64-3.49 (m, 1H), 2.90-2.85 (m, 1H), 2.81 (d, J=5.10 Hz, 3H), 2.40-2.29 (m, 2H), 1.97-1.88 (m, 2H); Mass Spectra: ESI: calculated: 178.11. found: MH$^+$ 179.18.

EXAMPLE 11

4-(Cbz-Leu-Amido)-6-Fluoro-5-Hydroxy-Hexanoic Acid Methylamide

To a solution of Cbz-Leu (0.371 g, 1.40 mmol) in THF (5.6 mL) was added EDCI (0.268 g, 1.40 mmol), HOBt (0.189 g, 1.40 mmol) and DMAP (0.085 g 0.70 mmol). The resulting mixture was stirred for 15 min, then a solution of 4-amino-6-fluoro-5-hydroxy-hexanoic acid methylamide (0.250 g, 1.40 mmol) in DMF (2 mL) was added slowly and the solution was stirred at room temperature overnight. The solvent was evaporated and the residue was diluted with ethyl acetate (100 mL). The solution was washed with water (4×20 mL), and the organic layer was dried over MgSO$_4$, concentrated and the residue was purified by flash chromatography (silica gel, gradient elution with EtOAc:Hexanes, 1:1 to iPrOH:CH$_2$Cl$_2$, 5:95) to give 0.180 g (32%) of the titled product as a colorless viscous oil. $^1$H NMR (CDCl$_3$): 7.35-7.29 (m, 5H), 6.93-6.90 (m, 1H), 6.62-6.58 (br s, 1H), 5.75-5.64 (m, 1H), 5.09 (s, 2H), 4.42-3.80 (m, 5H), 2.76-2.71 (m, 3H), 2.17-2.15 (m, 1H), 1.92-1.90 (m, 2H), 1.67-1.51 (m, 2H), 1.75 (m, 4H), 0.94 (d, J=6.6 Hz, 6H); Mass Spectra: ESI: calculated: 425.23. found: MH$^+$ 426.29.

EXAMPLE 12

4-(Cbz-Leu-Amido)-6-Fluoro-5-Oxo-Hexanoic Acid Methylamide

To a solution of 4-(Cbz-Leu-amido)-6-fluoro-5-hydroxy-hexanoic acid methylamide (0.180 g, 0.423 mmol) in CH$_2$Cl$_2$ (20 mL) at 0° C. was added Dess-Martin periodinane (0.538 g, 1.27 mmol) in small portions over 5 minutes. The resulting white mixture was allowed to equilibrate to room temperature and stirred for 1.5 h. The solvent was evaporated and the residue was diluted with ethyl acetate (200 mL), washed with water (5×20 mL), and the organic layer was dried over Na$_2$SO$_4$ and concentrated. The residue was purified by flash chromatography (silica gel, elution with EtOAc:Hexanes; 1:1) to give the title product (0.038 g, 21%) as a mixture of the cyclized form and open form based on $^1$H NMR. $^1$H NMR (CDCl$_3$): 7.36-7.33 (m, 5H), 7.08-7.00 (m, 0.5H), 6.94-6.90 (m, 0.5H), 5.50-5.38 (m, 1H), 5.09-5.07 (m, 3H), 4.55-4.05 (m, 4H), 2.93 (d, 3H), 2.48-2.43 (m, 2H), 1.93-1.88 (m, 3H), 1.68-1.53 (m, 4H), 0.93 (m, 6H); Mass Spectra: ESI: calculated: 423.22. found: MH$^+$ 424.28.

EXAMPLE 13

4-(Cbz-Ile-Amido)-6-Fluoro-5-Hydroxy-Hexanoic Acid Methylamide

The title compound was prepared similar to Example 11. From Cbz-Ile (0.298 g, 1.12 mmol) and 4-amino-6-fluoro-5-hydroxy-hexanoic acid methylamide (0.718 M solution in DMF, 0.200 g, 1.12 mmol) was obtained 0.090 g (19%) of the title compound as a white solid. $^1$H NMR (CDCl$_3$): 7.38-7.27 (m, 5H), 6.54-6.51 (m, 1H), 6.19 (br s, 1H), 5.27 (br s, 1H), 5.12-5.08 (m, 2H), 4.45-3.83 (m, 5H), 2.80-2.76 (m, 3H), 2.26-2.05 (m, 3H), 0.97-0.89 (m, 6H); Mass Spectra: ESI: calculated: 425.23. found: MH$^+$ 426.19.

EXAMPLE 14

4-(Cbz-Ile-Amido)-6-Fluoro-5-Oxo-Hexanoic Acid Methylamide

The title compound was prepared similar to Example 12. From 4-(Cbz-Ile-amido)-6-fluoro-5-hydroxy-hexanoic acid methylamide (0.090 g, 0.21 mmol) and Dess-Martin reagent (0.269 g, 0.634 mmol) was obtained 0.008 g (9%) of the title compound. $^1$H NMR (CDCl$_3$): 7.37-7.31 (m, 5H), 6.65-6.60 (m, 1H), 5.40-5.36 (m, 1H), 5.12-5.08 (m, 3H), 4.54.40 (m, 2H), 3.96-3.91 (m, 1H), 2.97-2.95 (m, 3H), 2.63-2.43 (m, 3H); Mass Spectra: ESI: calculated: 423.22. found: MH$^+$ 424.27.

EXAMPLE 15

4-(Cbz-Val-Amido)-6-Fluoro-5-Hydroxy-Hexanoic Acid Methylamide

The title compound was prepared similar to Example 11. From Cbz-Val (0.282 g, 1.12 mmol) and 4-amino-6-fluoro-5-hydroxy-hexanoic acid methylamide (0.718 M solution in DMF, 0.200 g, 1.12 mmol) was obtained 0.214 g (46%) of the title compound as a white solid. $^1$H NMR (CDCl$_3$): 7.36-7.34 (m, 5H), 6.75-6.64 (m, 1H), 6.30 (br s, 1H), 5.40-5.38 (m, 1H), 5.31 (s, 2H), 5.12 (s, 2H), 4.45-4.35 (m, 1H), 3.98-3.84 (m, 4H), 2.80-2.75 (m, 3H), 0.98-0.92 (m, 6H); Mass Spectra: ESI: calculated: 411.22. found: MH$^+$ 412.32.

EXAMPLE 16

4-(Cbz-Val-Amido)-6-Fluoro-5-Oxo-Hexanoic Acid Methylamide

The title compound was prepared similar to Example 11. From 4-(Cbz-Val-amido)-6-fluoro-5-hydroxy-hexanoic acid methylamide (0.070 g, 0.17 mmol) and Dess-Martin reagent (0.216 g, 0.510 mmol) was obtained 0.018 g (12%) of the title compound. $^1$H NMR (CDCl$_3$): 7.37-7.33 (m, 5H), 5.12-5.10 (m, 2H), 2.98-2.96 (m, 2H), 2.77-2.76 (m, 3H); Mass Spectra: ESI: calculated: 409.20. found: MH$^+$ 410.29.

EXAMPLE 17

3-(Cbz-Val-Amido)-5-Fluoro-4-Oxo-Pentanoic Acid Dimethylamide

To a solution of 3-(CBz-Val-amido)-5-fluoro-4-oxo-pentanoic acid (150 mg, 0.39 mmol) in THF (5 ml) was added a solution of 2.0 M dimethylamine in THF (0.2 ml, 0.4 mmol), EDCI (82.2 mg, 0.42 mmol) and HOBT (106 mg, 0.78 mmol) at 0° C. The resulting mixture was stirred for 2 h at 0° C., then was stirred at room temperature overnight. The solution was diluted with ethyl acetate (20 ml), washed with water (4×20 ml), and the organic layer was dried and evaporated. The residue was purified by chromatography over silica gel (hexane-EtOAc, 1:1 to pure EtOAc) to give 10 mg (6%) of the titled compound as a white solid. $^1$H NMR (DMSO-d$_6$): 8.36-8.30 (m, 1H), 7.45 (d, J=8.1 Hz, 1H), 7.33-7.29 (m, 5H), 5.45-5.09 (m, 2H), 5.03 (bs, 2H), 4.59-4.57 (m, 1H), 3.90-3.82 (m, 1H), 2.94 (bs, 3H), 2.84-2.73 (m, 4H), 1.97-1.93 (m, 1H), 1.25 (bs, 1H), 0.86-0.82 (m, 6H).

EXAMPLE 18

N,N-Dimethyl-4-Nitro-Butyramide

To a solution of methyl 4-nitrobutyrate (1.0 g, 6.80 mmol) in methanol (10 ml) was added 40% dimethylamine water solution (12.5 ml, 102 mmol). The solution was stirred at room temperature for 48 h, concentrated by vacuum, and diluted with ethyl acetate (20 ml). The organic layer was dried and evaporated. The residue was purified by flash chromatography over silica gel (Hexane-EtOAc, 1:1) to give the title product (0.99 g, 91%). $^1$H NMR (CDCl$_3$): 4.53 (t, J=6.6 Hz, 2H), 3.02-2.94 (m, 6H), 2.48-2.43 (m, 2H), 2.36-2.31 (m, 2H).

EXAMPLE 19

6-Fluoro-5-Hydroxy-4-Nitro-Hexanoic Acid Dimethylamide

To a cooled (−78° C.) solution of oxalyl chloride (0.9 ml, 9.63 mmol) in anhydrous dichloromethane (5 ml) was added anhydrous DMSO (1.4 ml, 19.38 mmol) dropwise and the reaction mixture was stirred for 15 min. A solution of 2-fluoroethanol (0.44 mL, 7.5 mmol) in dichloromethane (2 ml) was slowly added into the reaction flask. The reaction mixture was stirred for 15 min, then it was diluted with dichloromethane (60 ml), followed by addition of dry Et$_3$N (4.4 ml, 31.25 mmol). The reaction mixture was stirred for 15 min, then warmed to 0° C. and stirred at 0° C. for 2 h. To the reaction mixture was added a solution of N,N-dimethyl-4-nitro-butyramide (0.99 g, 6.25 mmol) in CH$_2$Cl$_2$ (5 ml). The reaction mixture was stirred at 0° C. for 3 h and then stirred at room temperature overnight. The mixture was concentrated and extracted with ethyl acetate. The organic layer were dried and evaporated. The residue was purified by silica gel (CH$_2$Cl$_2$/EtOAc=1:3) to give 1.23 g (89%) of the titled product as a colorless viscous oil. $^1$H NMR (CDCl$_3$): 4.98 (bs, 1H), 4.81-4.72 (m, 1H), 4.70-4.61 (m, 1H), 4.59-4.37 (m, 1H), 4.33-4.18 (m, 1H), 3.02-2.98 (m, 3H), 2.94-2.93 (m, 3H), 2.46-2.22 (m, 4H).

EXAMPLE 20

4-Amino-6-Fluoro-5-Hydroxy-Hexanoic Acid Dimethylamide

To a solution of 6-fluoro-5-hydroxy-4-nitro-hexanoic acid dimethylamide (1.22 g, 5.5 mmol) in MeOH (20 mL) was added Ranny Ni (about 500 mg), and the mixture was hydrogenated under 40-45 psi H$_2$ at room temperature for 6 h. The catalyst was removed. The MeOH solution was evaporated and the residue oil (0.92 g, yield 87%) was used without further purification. MS m/e 193 (M+1).

EXAMPLE 21

4-(Cbz-Leu-Amido)-6-Fluoro-5-Hydroxy-Hexanoic Acid Dimethylamide

To a solution of Cbz-Leucine (265 mg, 1 mmol) in THF (20 mL) was added EDCI (192 mg, 1 mmol), HOBT (135 mg, 1 mmol) and DMAP (61 mg 0.5 mmol). The resulting mixture was stirred for 10 min, then was added a solution of 4-amino-6-fluoro-5-hydroxy-hexanoic acid dimethylamide (192 mg, 1 mmol) in THF (2 mL), and it was stirred at room temperature overnight. The solvent was evaporated and the residue was diluted with ethyl acetate (20 mL). The solution was washed with water and the organic layer was dried and evaporated. The residue was purified by chromatography over silica gel (hexane-EtOAc, 1:1 to EtOAc/MeOH=3:1) to give 300 mg (68%) of the titled compound as a white solid. MS m/e 440 (M+1).

EXAMPLE 22

4-(Cbz-Leu-Amido)-6-Fluoro-5-Oxo-Hexanoic Acid Dimethylamide

To a solution of 4-(CBz-Leu-amido)-6-fluoro-5-hydroxy-hexanoic acid dimethylamide (300 mg, 0.68 mmol) in CH$_2$Cl$_2$ (20 ml) at 0° C. was added Dess-Martin periodinane (868 mg, 2.05 mmol). The resulting mixture was stirred at room temperature for 4 h, the solvent was evaporated and the residue was diluted with ethyl acetate (40 ml). It was washed with water and the organic layer was dried and concentrated. The residue was purified by column chromatography (EtOAc/MeOH 8:1) to give the title product (253 mg, 85%) as colorless oil. $^1$H NMR (acetone-$d_6$): 8.00-7.94 (m, 1H), 7.38-7.30 (m, 5H), 6.57 (m, 1H), 5.29-5.18 (m, 1H), 5.13-5.09 (m, 3H), 4.50-4.47 (m, 1H), 4.22-4.14 (m, 1H), 2.99-2.97 (m, 2H), 2.86-2.80 (m, 6H), 2.49-2.44 (m, 2H), 1.79-1.70 (m, 1H), 1.64-1.59 (m, 2H), 0.95-0.91 (m, 6H).

EXAMPLE 23

4-(Cbz-Ile-Amido)-6-Fluoro-5-Oxo-Hexanoic Acid Dimethylamide

The title compound was prepared in two steps similar to Example 21 and 22. $^1$H NMR (acetone-$d_6$): 7.95-7.93 (m, 1H), 7.38-7.29 (m, 5H), 6.43 (brs, 1H), 5.30-5.20 (m, 1H), 5.14-5.04 (m, 3H), 4.54-4.48 (m, 1H), 4.09-4.00 (m, 1H), 2.99-2.97 (m, 2H), 2.86-2.80 (m, 6H), 2.50-2.46 (m, 2H), 1.61-1.52 (m, 1H), 1.30-1.77 (m, 2H), 0.96-0.86 (m, 6H).

EXAMPLE 24

4-(Cbz-Val-Amido)-6-Fluoro-5-Oxo-Hexanoic Acid Dimethylamide

The title compound was prepared in two steps similar to Example 21 and 22. $^1$H NMR (acetone-$d_6$): 7.95 (brs, 1H), 7.38-7.29 (m, 5H), 6.43 (brs, 1H), 5.30-5.20 (m, 1H), 5.14-5.05 (m, 3H), 4.55-4.51 (m, 1H), 4.09-4.00 (m, 1H), 2.98-2.97 (m, 2H), 2.89-2.82 (m, 6H), 2.50-2.46 (m, 2H), 1.96-1.88 (m, 1H), 0.99-0.92 (m, 6H).

EXAMPLE 25

4-(Cbz-Gly-Amido)-6-Fluoro-5-Oxo-Hexanoic Acid Dimethylamide

The title compound was prepared in two steps similar to Example 21 and 22. $^1$H NMR (acetone-$d_6$): 7.90 (bs, 1H), 7.83-7.25 (m, 5H), 6.70 (bs, 1H), 5.40-5.02 (m, 2H), 5.10 (s, 2H), 4.55 (bs, 1H), 3.83 (d, 2H), 2.90-2.85 (m, 6H), 2.45 (m, 2H), 2.20-1.85 (m, 2H).

EXAMPLE 26

4-(Cbz-Ala-Amido)-6-Fluoro-5-Oxo-Hexanoic Acid Dimethylamide

The title compound was prepared in two steps similar to Example 21 and 22. $^1$H NMR ($CDCl_3$): 7.85 (bs, 1H), 7.78 (bs, 1H), 7.30-7.20 (m, 5H), 5.40 (m, 1H), 5.15 (bs, 3H), 4.98 (bs, 1H), 4.65 (bs, 1H), 4.25 (m, 1H), 2.98 (s, 3H), 2.95 (s, 3H), 2.60-2.25 (m, 2H), 2.25-2.00 (m, 2H), 1.40 (q, 3H).

EXAMPLE 27

Inhibition of SARS Coronavirus-Induced Cell Death

Compounds of this invention were tested in SARS-CoV infected Vero-cells, for the protective effects of compounds against SARS-CoV-induced cell death (cytopathic effect (CPE)), as a measurement of the inhibiting effects of compounds on the replication of SARS-CoV (Cinatl J, et al. Lancet, 2003, 361: 2045-6; and Tan E. L. C. et al. Emerg. Infect. Dis. 2004, 10: 581-586). SARS coronavirus infected and uninfected Vero 76 cells in microtiter plate wells are incubated for 72 h in the presence of serial dilutions of the test compound. Neutral red was added at the end of incubation, and after work up the optical density of the wells were measured at 450 nm. Antiviral activity of the test compound ($EC_{50}$, protection from virus-induced cell death) is measured by cells' ability to phagocytose neutral red, the ability of cells to uptake neutral red which measures the proportion of viable cells. Treatment of uninfected cells with test compounds were used to measure toxicity of the compound ($TC_{50}$).

Compound of Example 17 was found to have an $EC_{50}$ value of 0.0021 mg/mL, and $TC_{50}$ value of >0.050 mg/mL, which give an SI value of >24. The SI value is an indication of potential therapeutical index of the compound. Compound of Example 17 therefore has good anti-SARS coronavirus activity and has good potential therapeutical index.

Compound of Example 24 was found to have an $EC_{50}$ value of 0.02 μg/mL, and $TC_{50}$ value of >10 μg/mL, which give an SI value of >500. Compound of Example 24 therefore has high anti-SARS coronavirus activity and has a high potential therapeutical index.

In separate experiments with SARS-CoV infected Vero-cells, the compound of Example 24 was found to inhibit 100% of the cytopathic effect (CPE) of SARS-CoV at a concentration of 1 μM, and no toxicity was observed at the same concentration. Similarly, the compound of Example 12 was found to inhibit 100% of the CPE of SARS-CoV at a concentration of 1 μM, and no toxicity was observed at the same concentration. The compound of Example 7 was found to inhibit 94.5% of the CPE of SARS-CoV at a concentration of 1 μM, and no toxicity was observed at the same concentration.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound selected from the group consisting of:

Cbz-Leu-Gln-fluoromethyl ketone;

4-(Cbz-Val-Leu-amido)-6-fluoro-5-oxo-hexanoic acid dimethylamide;

4-(Cbz-Leu-amido)-6-Fluoro-5-oxo-hexanoic acid methylamide;

4-(Cbz-Ile-amido)-6-fluoro-5-oxo-hexanoic acid methylamide;

4-(Cbz-Val-amido)-6-fluoro-5-oxo-hexanoic acid methylamide;

3-(Cbz-Val-amido)-5-fluoro-4-oxo-pentanoic acid dimethylamide;

4-(Cbz-Leu-amido)-6-Fluoro-5-oxo-hexanoic acid dimethylamide;

4-(Cbz-Ile-amido)-6-Fluoro-5-oxo-hexanoic acid dimethylamide;

4-(Cbz-Val-amido)-6-Fluoro-5-oxo-hexanoic acid dimethylamide;

4-(Cbz-Ala-amido)-6-Fluoro-5-oxo-hexanoic acid dimethylamide; and 4-(Cbz-Gly-amido)-6-Fluoro-5-oxo-hexanoic acid dimethylamide;

or a pharmaceutically acceptable salt thereof.

* * * * *